United States Patent [19]
Woo et al.

[11] Patent Number: 5,645,696
[45] Date of Patent: Jul. 8, 1997

[54] PROCESS FOR PREPARING UNSATURATED CARBOXYLIC ACID ESTERS AND APPARATUS FOR PREPARING THE SAME

[75] Inventors: Boo Gon Woo; Kwang Ho Park; Hwa Myung Joo, all of Daejeon; Han Sun Lee, Seoul, all of Rep. of Korea

[73] Assignee: Lucky Ltd., Seoul, Rep. of Korea

[21] Appl. No.: 346,191

[22] Filed: Nov. 21, 1994

[51] Int. Cl.$^6$ .................................................. B01D 3/34
[52] U.S. Cl. ............................................. 203/60; 560/205
[58] Field of Search ................................. 560/205; 203/60

[56] References Cited

U.S. PATENT DOCUMENTS 3,579,309  5/1971  Sennewald et al. ................ 560/205

*Primary Examiner*—Paul J. Killos
*Attorney, Agent, or Firm*—Birch, Stewart, Kolasch & Birch, LLP

[57] ABSTRACT

The present invention relates to a process for continuously preparing unsaturated carboxylic acid esters by esterifying an (aliphatic) alcohol having 1 to 8 carbon atoms with an unsaturated carboxylic acid in the presence of a cation exchange resin catalyst, characterized in that the process is conducted by continuously circulating said reactants in contact with said catalyst from the top to the bottom through a reactor which is composed in the form of a fixed bed divided into 1 to 10 steps wherein each step comprises a catalyst bed, a filter and a air inlet, and has a thermal insulating outer wall, supplying a vaporizing heat for extraction of water, which is produced during the reaction, through a heat exchanger outside the reactor, circulating the reactants between the reactor and the heat exchanger by means of a circulating pump, contacting an azeotropic mixture of water vaporized by the heat exchanger and an alcohol with an alcohol circulating in a column tower or a raw alcohol supplied from an alcohol inlet located on the top of the column tower to recycle the high boiling component into the reactor and, at the same time, to transfer the light component to the upper part of the column in which the light component is condensed, separating the condensate into an organic layer and water in a decanter, and then recycling the organic layer into the reactor and removing the water produced during the reaction, and a novel apparatus for carrying out this process.

8 Claims, 1 Drawing Sheet

PROCESS FOR PREPARING UNSATURATED CARBOXYLIC ACID ESTERS AND APPARATUS FOR PREPARING THE SAME

BACKGROUND OF THE INVENTION

1. Field of the Invention

The present invention relates to an improved process for preparing unsaturated carboxylic acid esters and a novel apparatus for preparing the same. More particularly, the present invention relates to a process for esterification of an (aliphatic) alcohol having 1 to 8 carbon atoms and an unsaturated carboxylic acid by means of a cation exchange resin catalyst to prepare a corresponding unsaturated carboxylic acid ester, which provides a high yield of the desired ester product, inhibits the production of polymer by-products at the maximum level, maintains the conversion of the reactants at a constant rate regardless of the activity of catalyst and extends the life of catalyst.

2. Background Art

In the prior art, numerous methods have been utilized for esterification of said alcohol and unsaturated carboxylic acid to prepare a corresponding unsaturated carboxylic acid ester. However, those methods have some disadvantages in that a rate of conversion into an ester is low due to a low reaction rate and a relatively low equilibrium constant, and further the yield of ester products is low because etherification of alcohol and/or polymerization of (meth)acrylic acid may occur as a side reaction during esterification reaction.

A commercial method for preparing unsaturated carboxylic acid esters which is currently used in industrial scale is a method wherein a glass-lined batch reactor is used, an acid catalyst such as sulfuric acid or p-toluenesulfonic acid is used to increase the reaction rate and water produced during the reaction is continuously removed to induce the forward reaction. However, this method has some disadvantages in an economical view and an amount of waste water since the reactor is very expensive and the catalyst used in this reaction should be neutralized with a base such as NaOH.

Recently, some attempts have been made to provide a continuous process having an improved economics by using a strong cation exchange resin, which is formed by binding a sulfonic acid group ($SO_3H$) to a copolymer of polystyrene and DVB (divinyl benzene), as a catalyst for preparing said unsaturated carboxylic acid esters.

Particularly, Japanese Laid-open Patent Publication No. (sho) 49-54,326 discloses a reactor in the form of a fluidized bed, wherein the catalyst is suspended in the reactant by blowing a large amount of inert gas into the bottom of the reactor. However, this type of reactor has numerous disadvantages in that the vaccum condition cannot be easily maintained when the pressure within the reactor is reduced for extracting water produced during the reaction, and further the use of a large amount of gas has no economical merit.

In addition, Japanese Laid-open Patent Publication No. (sho) 63-17,844 discloses the use of a reactor in the form of a CSTR (continuous stirred tank reactor) for said esterification reaction. However, although this CSTR type of the reactor is useful in view of transfer of the reactants in the reactor and suspension of the catalyst, it has some disadvantages in that due to a weak mechanical strength of the cation exchange resin catalyst the catalyst can be readily broken and therefore the catalytic activity is lowered.

Further, Japanese Patent Publication No. (sho) 62-39,150 discloses a fixed bed-type reactor having an outer jacket, which can increase the reaction yield by vaporizing and extracting water produced during the reaction. However, the method using such type of reactor has also some disadvantages in that the catalyst present near the reactor wall can be deactivated with heat, the high temperature of the reactor wall dramatically enhances the polymerization reaction to produce a polymer of (meth)acrylic acid and its ester and further it is difficult to extract water produced during the reaction.

The present inventors have extensively studied to improve the disadvantages involved in the prior methods and reactors and found that in preparing unsaturated carboxylic acid esters by esterifying an (aliphatic) alcohol having 1 to 8 carbon atoms with an unsaturated carboxylic acid in the presence of a cation exchange resin catalyst, a method wherein water produced during the reaction can be continuously extracted to induce the forward reaction, the chances and times to contact the reactants with the cation exchange resin catalyst are increased and the area in which the catalyst is present is not directly heated, can be used to obtain a high yield of the desired product, a maximum inhibition of polymer production, a uniform conversion rate regardless of catalyst activity and a maximum extension of a life of the catalyst. Thus, we have completed the present invention.

Accordingly, it is an object of the present invention to provide an improved process for preparing unsaturated carboxylic acid esters from an (aliphatic) alcohol having 1 to 8 carbon atoms and an unsaturated carboxylic acid.

It is a further object of the present invention to provide a process for continuously preparing unsaturated carboxylic acid esters by esterifying an (aliphatic) alcohol having 1 to 8 carbon atoms with an unsaturated carboxylic acid in the presence of a cation exchange resin catalyst, characterized in that the process is conducted by continuously circulating said reactants in contact with the catalyst from the top to the bottom through a reactor which is composed in the form of a fixed bed divided into 1 to 10 steps wherein each step is composed of a catalyst bed, a filter and a air inlet, and has a thermal insulating outer wall, supplying a vaporizing heat for extraction of water, which is produced during the reaction, through a heat exchanger outside the reactor, circulating the reactants between the reactor and the heat exchanger by means of a circulating pump, contacting an azeotropic composition of water vaporized by the heat exchanger and an alcohol with an alcohol circulating in a column tower or a raw alcohol supplied from an alcohol inlet located on the top of a column tower to recycle the high boiling component into the reactor and at the same time to transfer the light component to the upper part of the column in which the light component is condensed, separating the condensate into an organic layer and water in a decanter, and then recycling the organic layer into the reactor and removing the water produced during the reaction.

Further, it is another object of the present invention to provide a novel apparatus suitably designed for carrying out the process of the present invention as defined above.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention and the drawing, in addition to the scope of the invention defined by the claims.

BRIEF DESCRIPTION OF THE DRAWING

For a thorough understanding of the nature and objects of the invention, reference should be had to the following detailed description taken in connection with the accompanying drawing in which.

DISCLOSURE OF INVENTION

Figure 1:
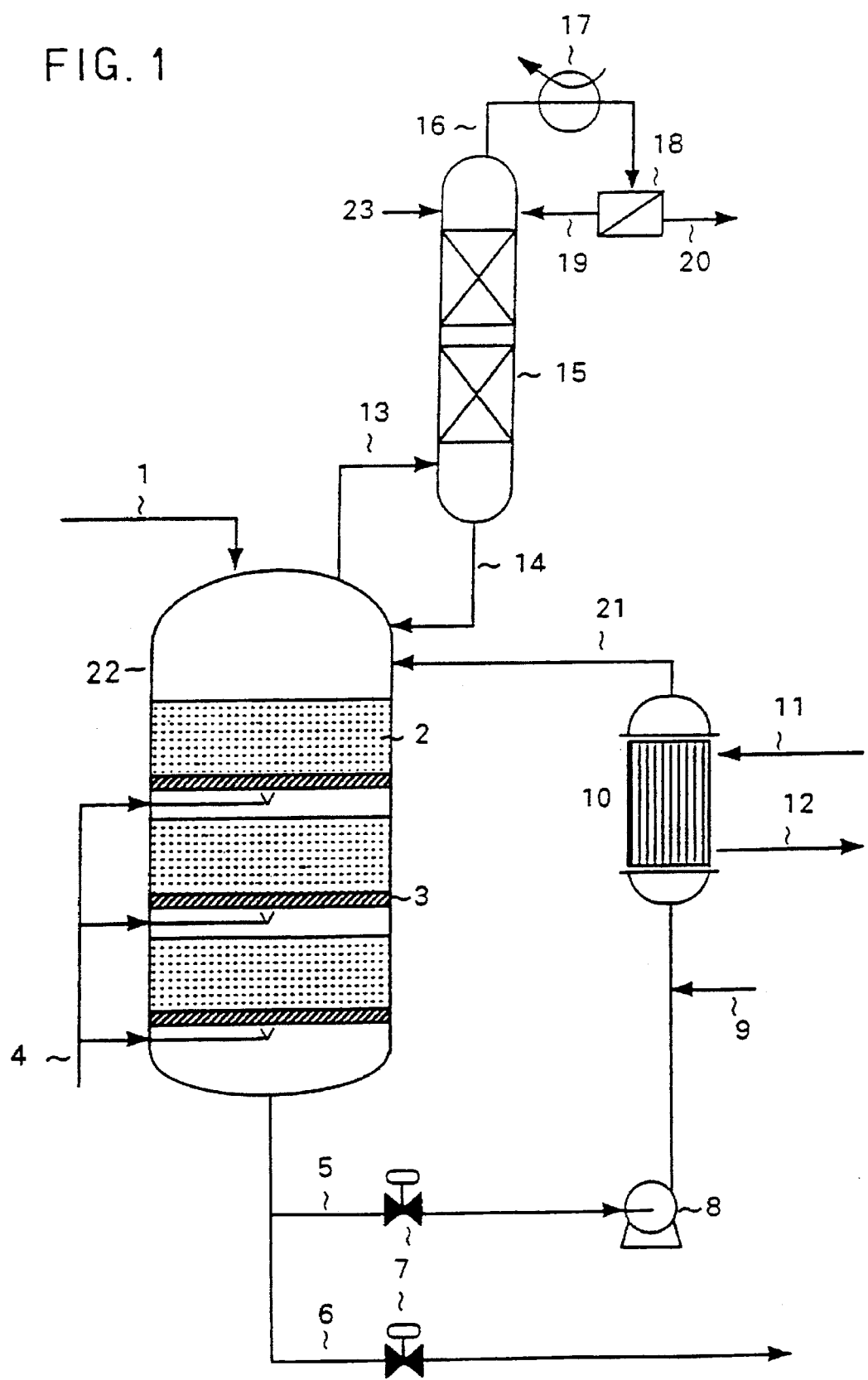
FIG. 1 is a schematic diagram of a reactor as the main part for carrying out the process according to the present invention, in which numerical symbols designate the following: 1,4, 5,6,9,11,12,13,14,16,19,20,21: pipes, 2: catalyst bed, 3: filter, pump, 8: circulating pump, 10:heat exchanger, 15: packed column, 17: condenser, 18: decanter, 22: reactor, 23: alcohol inlet.

In one aspect, the present invention relates to an improved process for preparing unsaturated carboxylic acid esters from an (aliphatic) alcohol having 1 to 8 carbon atoms and an unsaturated carboxylic acid.

Specifically, the present invention provide a process for continuously preparing unsaturated carboxylic acid esters by esterifying an (aliphatic) alcohol having 1 to 8 carbon atoms with an unsaturated carboxylic acid in the presence of a cation exchange resin catalyst, characterized in that the process is conducted by continuously circulating said reactants in contact with the catalyst from the top to the bottom through a reactor which is composed in the form of a fixed bed divided into 1 to 10 steps wherein each step is composed of a catalyst bed, a filter and a air inlet, and has a thermal insulating outer wall, supplying a vaporizing heat for extraction of water, which is produced during the reaction, through a heat exchanger outside the reactor, circulating the reactants between the reactor and the heat exchanger by means of a circulating pump, contacting an azeotropic composition of water vaporized by the heat exchanger and an alcohol with an alcohol circulating in a column tower or a raw alcohol supplied from an alcohol inlet located on the top of a column tower to recycle the high boiling component into the reactor and at the same time to transfer the light component to the upper part of the column in which the light component is condensed, separating the condensate into an organic layer and water in a decanter, and then recycling the organic layer into the reactor and removing the water produced during the reaction.

In another aspect, the present invention relates to a novel apparatus suitable for conducting the above process according to the present invention.

The present invention can be practiced using the above-mentioned process and a reactor system especially designed for the present invention and will be more specifically explained by referring to the drawing attached hereto.

The raw material comprising (aliphatic) alcohol and unsaturated carboxylic acid is introduced into the reactor through a pipe (1) and mixed with a high boiling reactant, which is introduced through a packed column (15) and a heat exchanger (10), at the upper part of the reactor. The mixture is allowed to react while running down a catalyst bed from up to down.

The reactor is in the form of a fixed bed divided into 1 to 10 steps, which comprises a catalyst bed (2) and a filter (3). An outer wall of the reactor is insulated from the heat so that it can maintain only the reaction temperature. The vaporizing heat for extraction of water produced during the reaction is supplied from a heat exchanger (10) outside the reactor.

To supply a calorie to the heat exchanger a steam or a heated solvent is supplied through a pipe (11). The total system is maintained under reduced pressure and the reaction temperature is kept at a bubbling point of the reactant.

When a phenolic polymerization inhibitor is used for inhibition of the polymer production, a small amount of air can also be supplied through pipes (4) and (9) for inhibition of polymerization. The reactants are circulated at a high flow rate between the reactor and the heat exchanger to conduct the continuous reaction and at the same time water produced during the reaction is continuously extracted by means of a heat exchanger (10). According to this procedure the desired unsaturated carboxylic acid ester is obtained at a high conversion rate. In this procedure, the conversion rate can be adjusted to some extent according to the flow rate of the reactant discharged from a circulating pump (8). Specifically, when the reactant is circulated in a great quantity, the reaction of the reactants in contact with the catalyst bed and the extraction of water produced during the reaction by the heat exchanger increase, and therefore, the conversion rate also increases. Such feature contributes to stably operate the procedure for purifying the product since the composition of the product after the reactants are passed through the reactor is uniformly maintained to some extent, regardless of the activity of catalyst.

The reactants are supplied to a circulating pump (8) through a pipe (5) to obtain the desired product through a pipe (6).

The catalyst is continuously separated from the reactants by means of a filter (3). The azeotropic composition of water vaporized by a heat exchanger (10) and alcohol is introduced into a column (15) together with some vaporized acid through a pipe (13) and then contacted with an alcohol circulating in the column tower. The resulting high boiling components such as acid are recycled into the reactor and the light components are transferred to the upper part of the column and then condensed in a condenser (17). The condensate is separated into an organic layer and an aqueous layer in a decanter (18). Then the organic layer is recycled into the column through a pipe (19) and the water produced during the reaction is removed through a pipe (20).

When the raw alcohol is supplied through an alcohol inlet (23) located on the top of a column tower (15), the raw alcohol absorbs (meth) acrylic acid present in the column (15) and therefore the residue at the tower top does substantially not contain (meth)acrylic acid. Accordingly, the aqueous layer obtained from the condensation and separation does substantially not contain (meth)acrylic acid and therefore, can be discharged without any special treatment. In addition, since (meth) acrylic acid is captured by alcohol component and then returned back to the column (15), any loss of (meth)acrylic acid does not occur.

The recycled alcohol and acid are introduced into the reactor through a pipe (14) and then participate again in the reaction. The amounts of the circulated raw materials and the product can be controlled by a control valve (7). Preferably, the circulated amount and the produced amount can be adjusted at the ratio of at least 10:1.

After the reactants pass through a heat exchanger (10), the azeotropic composition of low boiling water and alcohols or esters is vaporized and the remaining high boiling components are recycled into the reactor through a pipe (21).

A catalyst which can be used for this process is a strong cation exchange resin having an ionic exchange capacity of 1.2–2.05 meq/ml, for example, Diaion PK-228 (Mitsubishi Chemical Industries, Ltd.), XH-2071 (Rohm & Hass), Dowex monosphere 650 CH (Dow Chemical Co.), etc.

Although it has been known that the molar ratio of unsaturated carboxylic acid and alcohol is generally in the range of 1:0.5 to 1:2, the preferred molar ratio is near to 1:1 since an excessive amount of alcohol increases the conversion rate but requires a great energy for separation of alcohol during the purification procedure and an excessive amount of acid causes some problems related with its separation and the corrosion of the apparatus. In the present invention, the most preferred molar ratio of unsaturated carboxylic acid and alcohol is 1:0.8–1:1.3.

In the present invention, unsaturated carboxylic acids which can be used include acrylic acid, methacrylic acid, etc. The reaction temperature is preferably about 70° to 100° C., since too low temperature causes the low reaction rate whereas the high reaction temperature increases the by-product formation and the catalyst thermolysis. It is preferable to reduce the reaction pressure to 50 to 400 torr for convenient extraction of water produced during the reaction by the heat exchanger even under the reaction temperature. In order to prevent the formation of polymers during the reaction a phenolic polymerization inhibitor can be preferably used in an amount of about 100 to 500 ppm together with air.

The azeotropic composition of vaporized water and alcohols are contacted with a raw alcohol component supplied from the alcohol inlet located on the top of the column tower and then (meth)acrylic acid which is discharged together with water produced during the reaction is separated from the produced water and recovered. For recovery of the raw material, especially (meth)acrylic acid with the raw alcohol, an amount of the raw alcohol used for contact with the azeotropic composition is preferably 10 wt % or more, particularly 30 to 80 wt %, with repect to the alcohol supplied for the esterification reaction. When the amount of alcohol is lower than the above defined amount, it is difficult to recover (meth)acrylic acid.

The present invention will be more specifically explained by the following examples. However, it should be understood that the present invention is not limited to these examples in any manner and the unit m, KL, Atm, etc, used in the examples can be also converted into any other unit which is more generally used for commercial purpose.

EXAMPLE 1

A 3.5 L reactor made of glass was used in this example. In addition, a shell and a tube-type heat exchanger which are made of glass were attached to the reactor to which a removable glass filter was provided. A small magnetic pump was used as a circulating pump and the amount of the circulating reactants was adjusted by means of a flow controller.

First, butanol and acrylic acid were mixed in the molar ratio of about 1:1 to obtain the reactant having a fixed composition. To the reactant was added hydroquinone as a polymerization inhibitor in an amount of 0.05% based on the weight of acrylic acid and then the mixed reactant was stored at a resorvior. 2.8 L (based on the dried catalyst) of a catalyst such as Diaion PK-228, XH-2071 or Dowex monosphere 650CH which was previously dried at the ambient temperature of about 70° C. in an oven was packed in the reactor.

Some of the reactant was introduced into the reactor and then circulated for 2.5 hours without discharge of the reaction product. Then, after increasing the ambient temperature to about 75° C., the reactant was continuously introduced into the reactor at the flow rate of about 1 L/hr. together with a samll amount of air.

The pressure was maintained at about 150 torr from the beginning of the reaction. The water produced during the reaction was continuously vaporized by means of a heat exchanger and extracted through a distillation tower.

The flow rate of the circulated reactant was adjusted to about 25 L/hr.

After continuously operating the above procedure for 24 hours, the reaction product having the composition comprising about 0.26% of water, about 23.995% of butanol, about 63,942% of butylacrylate, about 10.55% of acrylic acid, about 1.18% of dibutyl ether, about 0.068% of dimeric acid and about 0.005% of dimeric acid ester was obtained. Thus, in this reaction the conversion rate based on acrylic acid was about 77.43% and the selectivity based on acrylic acid was about 99.3 mol %.

EXAMPLE 2

In this example, the same reactor as in Example 1 was used.

920 ml of Amberlyst 39C catalyst which was dried for 24 hours or more in an oven at 70° C. was packed in the reactor. To the raw material consisting of 30.70% of acrylic acid, 56.67% of 2-ethyl-hexanol, 12.15% of 2-ethyl-hexylacrylate and 0.48% of water was added the same amount of hydroquinone as in Example 1 and the mixture was introduced at once into the reactor having a suitable size and circulated while increasing the temperature to 80° C. Then, the reaction was conducted for 1 hour and 40 minutes under the fixed pressure of 77 mmHg while discharging water through the distillation tower and then the raw material and small amount of air were continuously introduced into the reaction system. The general inflow rate of the raw material was 687.84 g/hr. 30% of 2-ethyl-hexanol of the raw material to be introduced into the reaction system was introduced from the upper part of the distillation tower for water separation. The liquid level in the reactor was uniformly maintained such that the residual time should become 100 minutes and the flow rate of the circulated reactant was fixed at the level of 10 L/hr.

After continuously operating the above procedure for 24 hours, the reaction product having the composition comprising 13.49% of acrylic acid, 25.62% of 2-ethyl-hexanol, 60.16% of 2-ethyl-hexylacrylate, 0.52% of water, 0.05% of dimeric acid, 0.15% 2-ethyl-hexyl ester of dimeric acid and 0.01% of 2-ethyl-hexylpropionate was obtained. Thus, in this reaction the conversion rate based on acrylic acid was about 57.59% and the selectivity based on acrylic acid was about 99.57 mol %.

In addition, the outflow rate of acrylic acid from the upper part of the distillation tower was too little to analyze.

EXAMPLE 3

In this example, the same reactor as in Example 1 was used.

920 ml of Amberlyst 39C catalyst which was dried for 24 hours or more in an oven at 70° C. was packed in the reactor. To the raw material consisting of 34.52% of acrylic acid and 65.48% of 2-ethyl-hexanol was added the same amount of hydroquinone as in Example 1 and the mixture was introduced at once into the reactor having a suitable size and circulated while increasing the temperature to 80° C. Then, the reaction was conducted for 1 hour and 40 minutes under the fixed pressure of 77 mmHg while discharging water through the distillation tower and then the raw material and small amount of air were continuously introduced into the reaction system. The general inflow rate of the raw material was 698.46 g/hr. 30% of 2-ethyl-hexanol of the raw material to be introduced into the reaction system was introduced from the upper part of the distillation tower for water separation. The liquid level in the reactor was uniformly maintained such that the residual time should become 100 minutes and the flow rate of the circulated reactant was fixed at the level of 10 L/hr.

After continuously operating the above procedure for 24 hours, the reaction product having the composition comprising 12.63% of acrylic acid, 25.96% of 2-ethyl-hexanol, 60.65% of 2-ethyl-hexyl acrylate, 0.50% of water, 0.08% of dimeric acid, 0.16% 2-ethyl-hexyl ester of dimeric acid and 0.02% of 2-ethyl-hexylpropionate was obtained. Thus, in this reaction the conversion rate based on acrylic acid was about 65% and the selectivity based on acrylic acid was about 99.52 mol %.

In addition, the outflow rate of acrylic acid from the upper part of the distillation tower was too little to analyze as in Example 2.

Although this invention has been described in its preferred form with a certain degree of particularity, it is appreciated by those skilled in the art that the present disclosure of the preferred form has been made only by way of examples and that numerous changes in the details of the construction, combination and arrangement of parts may be resorted to without departing from the spirit and scope of the invention.

What is claimed is:

1. An apparatus for continuously preparing unsaturated carboxylic acid esters with an esterifying reaction, wherein an (aliphatic) alcohol reactant having 1 to 8 carbon atoms is reacted with an unsaturated carboxylic acid reactant in the presence of a cation exchange resin catalyst, said apparatus comprising:

a fixed bed reactor divided into 1 to 10 steps, wherein each step comprises a catalyst bed, a filter and an air inlet, and wherein said reactor has a thermal insulating outer wall and a top and a bottom portion, a column tower having a top and a bottom portion, wherein the bottom portion of the column tower is connected to the top portion of said reactor, heat exchanging means outside said reactor for supplying a vaporizing heat for extracting water that is produced during the reaction, circulating means for circulating the reactants between the reactor and the heat exchanging means, contacting means for contacting an azeotropic composition of an alcohol and water vaporized by the heat exchanging means with either:
   (i) an alcohol circulating in said column tower, or (ii) a raw alcohol supplied from an alcohol inlet located on the top portion of said column tower, to thereby recycle a high boiling point component of the reaction mixture into the top portion of the reactor and, at the same time, to transfer a low boiling point component of the reaction mixture to the top portion of the tower column, where the low boiling point component condenses and forms a condensate, separating means for separating the condensate into an organic layer and a water layer, recycling means for recycling the organic layer into the top portion of the reactor, and removing means for removing the water produced during the reaction;

provided that the process is conducted by continuously circulating said reactants in contact with said catalyst from the top portion to the bottom portion of the reactor.

2. The apparatus according to claim 1, wherein the unsaturated carboxylic acid is acrylic acid or methacrylic acid.

3. The apparatus according to claim 1, wherein the molar ratio of unsaturated carboxylic acid and alcohol is about 1:0.8 to 1:1.3.

4. The apparatus according to claim 1, wherein the esterifying reaction is carried out at a temperature of about 70° to 100° C.

5. The apparatus according to claim 1, wherein the esterifying reaction is carried out at a pressure of about 50 to 400 torr.

6. The apparatus according to claim 1, wherein the esterifying reaction is carried out in the presence of a polymerization inhibitor that is a phenolic inhibitor used in an amount of about 100 to 500 ppm.

7. The apparatus according to claim 1, wherein the amount of alcohol circulating in the column tower is at least 10 wt % of the amount of alcohol supplied for the esterification reaction.

8. The apparatus according to claim 1, wherein the cation exchange resin catalyst has an ionic exchange capacity of 1.2–2.05 mEq/ml.

* * * * *